United States Patent [19]

Recker

[11] Patent Number: 4,870,054
[45] Date of Patent: Sep. 26, 1989

[54] TREATMENT FOR OSTEOPOROSIS USING GRF OR A BIOLOGICALLY ACTIVE ANALOG THEREOF

[76] Inventor: Robert R. Recker, 3309 S. 116th St., Omaha, Nebr. 68144

[21] Appl. No.: 80,110

[22] Filed: Jul. 31, 1987

Related U.S. Application Data

[63] Continuation-in-part of Ser. No. 780,949, Sep. 27, 1985, Pat. No. 4,710,382.

[51] Int. Cl.⁴ .............................................. A61K 37/36
[52] U.S. Cl. ........................................ 514/12; 424/43
[58] Field of Search ...................... 514/12; 424/43, 108

[56] References Cited

U.S. PATENT DOCUMENTS

| | | | |
|---|---|---|---|
| 4,153,689 | 5/1979 | Hirai | 514/3 |
| 4,476,116 | 10/1984 | Anik | 514/15 |
| 4,518,586 | 5/1985 | Rivier | 530/324 |
| 4,617,149 | 10/1986 | DiMarchi | 530/324 |
| 4,710,382 | 12/1987 | Recker | 514/12 |

OTHER PUBLICATIONS

Vale, *Endocrinology*, 112, No. 4, 1553 (1983).
Lance, Biochemical and Biophysical Research Communications, 119, No. 1, 265–272 (1984).

*Primary Examiner*—Delbert R. Phillips
*Assistant Examiner*—F. T. Moezie
*Attorney, Agent, or Firm*—Zarley, McKee, Thomte, Voorhees & Sease

[57] ABSTRACT

A method of treating osteoporosis, especially postmenopausal osteoporosis, by administering on a periodic but regular basis to a patient growth hormone releasing factor, GRF(1-44)-NH$_2$, or a biologically active analog thereof, and continuing the administration until bone mass increases and the patient's calcium balance becomes positive and indicates a mineral accumulation in the skeleton.

10 Claims, No Drawings

TREATMENT FOR OSTEOPOROSIS USING GRF OR A BIOLOGICALLY ACTIVE ANALOG THEREOF

CROSS-REFERENCE TO A RELATED APPLICATION

This application is a continuation-in-part of application Ser. No. 780,949, filed Sept. 27, 1985, now U.S. Pat. No. 4,710,382.

BACKGROUND OF THE INVENTION

In the past 15 years, the physiology of pituitary function has become better understood. The pituitary gland secretes several hormones which in turn control secretion of other glands such as the adrenal, the thyroid, and the reproductive organs. In recent times, a series of pituitary releasing hormones have been discovered, and characterized. The most recent of these is growth hormone releasing factor GRF(1-44)-$NH_2$. This discovery occurred in 1982 when two investigators independently, but almost simultaneously, reported the presence of a substance occurring in a pancreatic tumor which caused a clinical syndrome called acromegaly. In their respective journal articles, they reported that the tumors were found to contain a peptide consisting of 44 amino acids, which when purified and injected into animals or humans was found to stimulate growth hormone production intensively, *Science*, Vol. 218, Nov. 5, 1982, pp. 585–87 and *Nature*, Vol. 300, Nov. 18, 1982, pp. 276–78. Recently, some researchers have successfully, synthetically synthesized growth hormone releasing factor, and very recently it has been produced by genetic engineering procedures using bacterial cultures. For literature relating to synthetic production of growth hormone releasing factor see Gelato, M. C. et al., 1983, "The Effects of Growth Hormone Releasing Factor in Man," *Journal of Clinical Endrocrinology and Metab.*, 57674.

Growth hormone releasing hormone factor is a peptide of 44 amino acids. There are analogs containing 27–40 amino acids. It is one of a group of peptides secreted by the hypothalamus, and it normally stimulates pituitary growth hormone release. It is important in normal growth and development during childhood.

Recently, it has been reported that GRF(1-44)-$NH_2$ may have some promise in the treatment of growth hormone deficiency (see *Journal of Clinical Endrocrinology and Metab.*, 59:1, 1984 and *Journal of Clinical Endrocrinology and Metab.*, 58:1043, 1984). However, GRF(1-44)-$NH_2$ has not yet been marketed or suggested for any specific clinical disease treatment. It has been suggested as likely to be useful for testing pituitary function by using doses to stimulate pituitary secretion of growth hormone factor. The theory being that in the event it does not so stimulate, one knows that the pituitary gland is not functioning properly. However, when used to test pituitary function GRF(1-44)-$NH_2$ is administered intravenously by a single bolus injection and blood levels of growth hormone are measured in serum specimens obtained at approximately half hour intervals for four hours. If growth hormone levels fail to rise, then the presumption is made that the pituitary gland is incapable of secreting growth hormone. This is a single dose for diagnostic purposes, not a periodic and regular treatment pattern.

Postmenopausal osteoporosis is defined as the presence of severe loss of bone, with or without fractures, in women who are past memopause. Bone loss without fractures has been termed osteopenia although many refer to bone loss with or without fractures as osteoporosis. The bone loss is from The "inside" of the skeleton rather than a shrinkage of the outer volume of the skeleton. The skeleton "hollows out." For many years, physicians have been searching for an agent that will cause reaccumulation of this lost bone so that risk of fracture is diminished. It is a major public health problem affecting millions of postmenopausal women. Almost half of the Caucasian women in the United States can be expected to suffer fractures from osteoporosis before they die.

This invention has as its primary objective the treatment of osteoporosis, preferably postmenopausal osteoporosis with GRF(1-44)-$NH_2$ until the patient's bone mass increases and the patient's calcium balance becomes positive, indicating mineral accumulation in the skeleton.

Another objective of the present invention is to provide a method of treatment of postmenopausal osteoporosis with GRF(1-44)-$NH_2$, or a biologically acceptable analog thereof.

An even further objective of the present invention is to provide a method of successfully administering GRF(1-44)-$NH_2$ or biologically acceptable analogs thereof to enhance their effect in reversing bone mass loss in postmenopausal patients.

A still further objective of the present invention is to provide a nasal insufflation composition which can be used for treatment of osteoporosis.

The method and means of accomplishing each of the above objectives, as well as others will become apparent from the description of the invention which follows hereinafter.

It goes without saying that certain modifications to the growth hormone releasing factor itself, or to the composition containing the same, may be made without departing from the spirit or scope of the present invention. Put another way, modifications both in the formula to provide some related analogs of the growth release factor, and in the composition to provide either other forms of administration, or other pharmaceutically acceptable related compositions may be made. These modifications are included in the scope of this invention.

SUMMARY OF THE INVENTION

Osteoporosis, preferably postmenopausal osteoporosis, is treated by administering on a periodic but regular basis to a patient a growth hormone releasing effective amount of GRF(1-44)-$NH_2$, or a biologically acceptable analog thereof, and monitoring the skeletal formation. The administration continues until the bone mass increases and the patient's calcium balance becomes positive, indicating mineral accumulation in the skeleton.

DETAILED DESCRIPTION OF THE INVENTION

In osteoporosis, growth plates epiphyses have closed in these adults and in the case of postmenopausal osteoporosis, as heretofore explained, there is a loss of bone in the skeleton leaving what might be described as "hollow bones." These hollow ones are highly susceptible to fracture. The treatment process of this invention takes advantage of the fact that the adult skeleton of low mass will respond to growth hormone by reexpanding its mass. Growth plates are not involved and therefore the treatment should last for several years, perhaps with repeated courses of treatment if bone loss again resumes after treatment is stopped. The purpose of the treatment is to restore lost bone to the skeleton, thereby preventing fractures.

GRF(1-44)-NH$_2$ is an attractive molecule for treatment of postmenopausal osteoporosis because the molecule is relatively small and simple and therefore can be effective when given by nasal insufflation, using an appropriate vehicle. It is small enough to be absorbed across the nasal mucous membrane and reach the circulation intact in relatively high concentration. Since it is necessary to give the growth hormone releasing factor repeatedly over a long period of time, this route of administration, i.e. nasal insufflation, is preferred and has great convenience and comfort over parenteral administration by techniques such as intramuscular, subcutaneous or intravenous administration which require repeated injections with a needle and syringe. It is, however, possible that such parenteral means of dosage administration may be used, although less preferred. It is also conceivable that growth hormone releasing factor may be given by pill or capsule, but to date no such pills or capsules have yet been developed. Nasal insufflation is preferred because of its rapid absorption into the systemic system of the body.

The dosage level will vary, depending upon the age, weight and size of the patient, but typically satisfactory results may be obtained when administered at levels of from 1 μg/day up to about 100 μg/day. A preferred dosage level is from 1 μg/day to about 5 μg/day. Shortly after administration, the patient may observe a flushed feeling, but this dissipates quickly.

Administration should continue until clinical evaluation reveals that bone mass has increased, preferably to within the range of from about 10% increase to about 15% increase. For administration by nasal insufflation, insufflation should occur from about 1 to about 6 times daily.

While the foregoing description has primarily been with reference to the naturally occurring growth hormone releasing factor, GRF(1-44)-NH$_2$, it should be noted that biologically active analogs thereof may also be used. There are several analogs of GRF(1-44)-NH$_2$ which have biological activity, but are somewhat less potent. It is contemplated that those analogs which are biologically active may also be used in the treatment process of the invention. They may be selected from the group consisting of GRF(1-44)-NH$_2$, GRF(1-40)-OH, GRF(1-40)-NH$_2$, GRF(1-32)-NH$_2$, GRF(1-39)-NH$_2$, GRF(1-40)-Phe-NH$_2$, GRF(1-40)-Phe-OH, GRF(1-40)-Phe-Gln-NH$_2$, and GRF(1-27)-NH$_2$.

The following example is set forth to provide a sample protocol for administraton of GRF(1-44)NH$_2$, or its biologically active analogs.

EXAMPLE

The patient protocol would be a white female past the age of menopause with low bone mass. The patient may or may not have fractures at the time treatment is undertaken. Necessarily prior to the treatment the patient must have a clinical evaluation ruling out other causes of low bone mass, with the diagnosis of osteoporosis being established by measurement of bone mass by current methods such as single photon absorptiometry, dual photon absorptiometry, or CT scanning of the spine.*

*Single photon absorptiometry of the wrist would measure about 0.400 grams of calcium per cm of radius and dual photon absorptiometry of the spine would measure about 25 grams in the second, third and fourth lumbar vertebrae combined.

Growth hormone releasing factor is administered by the preferred nasal insufflation route, at levels ranging from 1 to 6 times daily at a total dose of 5 μg day. This treatment is continued for a period of from 2 to 5 years during which time bone mass measurements are repeated at intervals of from 6 to 12 months. Treatment should be continued until there is an increase in bone mass of from 10% to about 15%.** Thereafter, the patient's bone mass is periodically checked, perhaps once per year, and treatment reinstated with similar doses with the identical protocol if there is bone less shown.

**Single photon absorptiometry of the radium would be about 0.460 gm/cm and dual photon absorptiometry would measure about 28.8 grams of calcium in the second, third and fourth lumbar vertebrae after successful treatment.

The formulation for the solution for nasal insufflation of GRF(1-44)-NH$_2$ could also employ the biologically active analogs. A typical formulation for the nasal spray in each milliliter would contain 100 μg of GRF(1-44)-NH$_2$ releasing factor, plus 5 mg of chlorobutanol, 9 mg of sodium chloride and with hydrochloric acid added to adjust the pH to approximately 4. For other typical compositions of nasal inhalants and carriers for the same, see *Handbook of Non-Prescription Drugs* (7th Ed., 1982).

The nasal insufflation route is preferred, but others that may be used include parenteral route, rectal suppositories, etc.

When in the above example a naturally occurring growth hormone releasing factor, GRF(1-44)-NH$_2$ is replaced with biologically active analogs thereof, substantially similar results are obtained. In particular the bioloigically active analogs of GRF(1-44)-NH$_2$ which can be used in the treatment process of this example are the following: GRF(1-40)-OH, GRF(1-40)-NH$_2$, GRF(1-32)-NH$_2$, GRF(1-39)-NH$_2$, GRF(1-40)-Phe-NH$_2$, GRF(1-40)-Phe-OH, GRF(1-40)-Phe-Gln-NH$_2$, and GRF(1-27)-NH$_2$.

It can therefore be seen from this example that the substituted analogs have the same active capability as the naturally occurring growth hormone releasing factor in that they, too, form an effective treating agent for osteoporosis, postmenopausal osteoporosis, and increasing of skeletal mass by mineral accumulation in the skeleton.

What is claimed is:

1. A method of treating osteoporosis, comprising:
   administering to a patient an effective amount of human GRF(1-44)-NH$_2$ analog selected from the group consisting of GRF(1-40)-OH, GRF(1-40)-NH$_2$, GRF(1-32)-NH$_2$, GRF(1-39)-NH$_2$, GRF(1-40)-Phe-NH$_2$, GRF(1-40)-Phe-OH, GRF(1-40)-Phe-Gln-NH$_2$, and GRF(1-27)-NH$_2$ to stimulate the pitutary growth hormone release and contionuing said administration until bone mass increases and patients calcium balance becomes positive and indicates mineral accumulation in the skeleton.

2. The method of claim 1 wherein the amount of GRF(1-44)-NH$_2$ analog administered is from about 1 μg/day to about 100 μg/day.

3.

3. The method of claim 2 wherein the amount administered is from about 1 μg/day to about 5 μg/day.

4. The method of claim 1 wherein said treatment continues until bone mass increases to within the range of from about 10% to about 15%.

5. The method of claim 1 wherein the method of administration is nasal insufflation.

6. The method of claim 1 wherein the method of administration is parenteral.

7. The method of claim 1 wherein said osteoporosis is old age osteoporosis.

8. The method of claim 1 wherein said osteoporosis is postmenopausal osteoporosis.

9. The method of claim 5 wherein said nasal insufflation occurs from 1 to 6 times daily.

10. A method of treating postmenopausal osteoporosis comprising:
administering human GRF(1-44)-NH$_2$ analog selected from the group consisting of GRF(1-40)-OH<GRF(1-40)-NH$_2$, GRF(1-32)-NH$_2$, GRF(1-39)-NH$_2$, GRF(1-40)-Phe-NH$_2$, GRF(1-40)-Phe-OH, GRF(1-40)-Phe-Gln-NH$_2$, amd GRF(1-27)-NH$_2$, said administration occurring by nasal insufflation; and
continuing said administration until bone mass of said patient increases from about 10% to about 15%, and the patient's calcium balance becomes positive indicating mineral accumulation in the skeleton.

* * * * *